United States Patent
Tafas et al.

(10) Patent No.: US 8,385,625 B2
(45) Date of Patent: Feb. 26, 2013

(54) SYSTEM FOR DETECTING INFECTIOUS AGENTS USING COMPUTER-CONTROLLED AUTOMATED IMAGE ANALYSIS

(75) Inventors: Triantafyllos P. Tafas, Rocky Hill, CT (US); Michael Kilpatrick, West Hartford, CT (US); Petros Tsipouras, Madison, CT (US)

(73) Assignee: IKONISYS, Inc., New Haven, CT (US)

( * ) Notice: Subject to any disclaimer, the term of this patent is extended or adjusted under 35 U.S.C. 154(b) by 0 days.

(21) Appl. No.: 13/188,714

(22) Filed: Jul. 22, 2011

(65) Prior Publication Data

US 2012/0020542 A1    Jan. 26, 2012

Related U.S. Application Data

(63) Continuation of application No. 13/022,348, filed on Feb. 7, 2011, now Pat. No. 7,991,213, which is a continuation of application No. 12/052,898, filed on Mar. 21, 2008, now Pat. No. 7,885,449, which is a continuation of application No. 10/543,270, filed as application No. PCT/US02/17586 on Jun. 4, 2002, now abandoned.

(60) Provisional application No. 60/295,587, filed on Jun. 4, 2001.

(51) Int. Cl.
*G06K 9/00* (2006.01)
*C12Q 1/00* (2006.01)
*A61B 5/00* (2006.01)
*A61B 8/00* (2006.01)
*A61B 10/00* (2006.01)

(52) U.S. Cl. .............................. 382/133; 435/4; 424/9.6

(58) Field of Classification Search .......... 382/128–134; 435/4, 7.2–7.37; 424/9.6
See application file for complete search history.

(56) References Cited

U.S. PATENT DOCUMENTS

| | | | |
|---|---|---|---|
| 6,548,259 B2 * | 4/2003 | Ward et al. ................... | 435/6.11 |
| 2004/0033555 A1 * | 2/2004 | Anderson et al. .............. | 435/34 |

* cited by examiner

*Primary Examiner* — Aaron W Carter
(74) *Attorney, Agent, or Firm* — Kelley, Drye and Warren LLP (57) ABSTRACT

A method for providing quantitative information regarding the extent of infection of host cells by an infectious agent. A microscope image of a specimen of a bodily fluid is analyzed using image processing techniques to quantify the percentage of the area of the specimen that is infected.

4 Claims, 4 Drawing Sheets

SYSTEM FOR DETECTING INFECTIOUS AGENTS USING COMPUTER-CONTROLLED AUTOMATED IMAGE ANALYSIS

CROSS-REFERENCE TO RELATED APPLICATION

This is a continuation application of U.S. patent application Ser. No. 13/022,348, filed Feb. 7, 2011, and issued as U.S. Pat. No. 7,991,213 on Aug. 2, 2011, which is a continuation of U.S. patent application Ser. No. 12/052,898 filed Mar. 21, 2008, now U.S. Pat. 7,885,449, which is a continuation of U.S. patent application Ser. No. 10/543,270, filed Jun. 2, 2006, now abandoned which is a National Stage of International PCT Application Number PCT/US02/17586 filed on Jun. 4, 2002 and published as WO02/098280 on Dec. 12, 2002, which claims priority to U.S. Provisional Patent Application No. 60/295,587 filed Jun. 4, 2001, each of which is incorporated herein by reference.

FIELD OF THE INVENTION

The present invention relates to computer controlled methods and apparatus for detecting or detecting and quantifying an infectious agent in a biological sample. The identifying and/or quantitative data obtained are useful in making a diagnosis or prognosis of diseases, including diseases classically deemed "non-infectious." In one aspect, the invention relates to computer controlled methods and systems for identifying an infected host, animal or plant cell in a field of cells and thereby providing information useful in making a disease diagnosis or a prognosis of disease susceptibility based on identification of an infected animal cell. In another aspect, the invention relates to computer controlled methods and systems for quantification of infected host, e.g., animal or plant cell(s) in a biological sample, thereby providing information useful in making a disease diagnosis or a prognosis of disease susceptibility based on the quantification of infected cell(s). The quantification may be determination of the number of infected animal cells, or of the extent to which the cells are infected (i.e., the number of infectious agents in an infected cell) or determination of both numbers. The quantitative information also is useful to assess therapeutic efficacy of treatment of disease.

In one important embodiment, the invention relates to quantification of *Chlamydia* infected mononuclear phagocyte(s) in a blood or tissue sample to provide information useful to make a diagnosis or prognosis of susceptibility of vascular or coronary disease.

In another important embodiment, the invention relates to quantification of *Chlamydia* infected mononuclear phagocyte(s) in a biological sample to provide information helpful for or useful to make a diagnosis (or prognosis) of a central nervous system (CNS) disease or disorder.

In yet another aspect, the present invention relates to computer controlled methods and systems for detecting and quantifying an infectious agent "free floating" in a biological sample to provide data useful in making a diagnosis or prognosis of disease or disorders, including diseases classically deemed "non-infectious".

BACKGROUND OF THE INVENTION

Citation or identification of any reference in this section or any section of this application shall not be construed as an admission that such reference is available as prior art to the present invention.

Atherosclerosis is the main underlying cause of coronary heart disease and is characterized by the deposit of lipid containing plaques on endothelium of large and medium sized arteries. Atherosclerosis is thought to be initiated at dysfunctional vascular endothelium when normal laminar blood flow is disrupted. Many systemic and local factors may cause dysfunctional endothelium and lead to or trigger an inflammatory response in the vessel wall. Multiple cell types can mediate this process, including monocyte-derived macrophages. Drexler, H. 1997. Prog. Cardiovasc. Dis. 39:287. The dysfunctional endothelium allows passage of low density lipoprotein ("LDL") cholesterol and expresses multiple adhesion molecules for platelets and inflammatory cells. The LDL cholesterol undergoes partial oxidation and causes further endothelial dysfunction while monocytes penetrate the endothelium, differentiate into macrophages, and take up oxidized LDL cholesterol. The resulting lipid-laden macrophages, also known as foam cells, accumulate in the atherosclerotic lesion and ultimately may rupture to release oxidized LDL cholesterol and cytotoxic enzymes. This triggers fibroproliferative responses from vascular smooth muscle cells and leads to the development of atherosclerotic plaques. Fuster et al. 1992. N. Engl. J. Med. 326:310; Stary, H. C. 1989. Arteriosclerosis 99:1-19.

Studies have shown Herpes viruses, such as Herpes simplex virus and Cytomegalovirus ("CMV"), can increase the risk of developing heart disease. Roivainen et al. 2000, Circulation 101(3):252. For example, elevated CMV antibody titres are associated with the presence of atherosclerosis. Melnick et al. 1990. JAMA 263:2204; Danesh et al. 1997, Lancet 350:430; Cheng et al. 2000, Expert Opin. Investig. Drugs 9(11):2505. Based on pathological data demonstrating CMV DNA sequences and viral inclusions in atherosclerotic lesions, 75 consecutive patients undergoing directional coronary atherectomy for coronary disease were studied to see if a link between CMV infection and arterial disease exists. The results showed that patients who were seropositive for CMV prior to the procedure have a greater than five-fold increased rate arterial disease. Zhou et al. 1996. N. Engl. J. Med. 335: 624.

A mechanism by which CMV may affect atherosclerosis hinges on the mononuclear phagocyte. CMV integrates into mononuclear cell precursor DNA thereby causing circulating monocytes to be a vector for delivering virus to sites of vessel inflammation. Guetta et al. 1997. Circ. Res. 81:8. Macrophages have been shown to be a similar source of circulating HUV in patients with AIDS. Orenstein et al. 1997. Science 276:1857. Studies have demonstrated that endothelial cells, smooth muscle cells, and oxidized LDL cholesterol can activate CMV viral replication in infected mononuclear phagocytes which can lead to macrophage, endothelial cell, and vascular smooth muscle cell infection with CMV. CMV infected smooth muscle cells may then obtain growth advantages and contribute to proliferative responses in atherosclerosis due to CMV induced changes in expression of regulatory proteins. Speir et al. 1994. Science. 265:391.

A link between atherosclerosis and *Helicobacter pylori* has also been shown. *H. pylori* is a Gram-negative rod which has been implicated in the development of peptic ulcers, gastric carcinoma, and low-grade B cell lymphomas of the gastrointestinal tract. Schussheim et al. 1999, Drugs 57:283. An association of *H. pylori* infection with coronary disease has been suggested in which seropositivity conferred a two-fold increased risk of coronary artery disease among nearly 200 men. Mendall et al. 1994. Br. Heart J. 71:437; Danesh et al. 1997, Lancet 350:430; Cheng et al. 2000, Expert Opin. Investig. Drugs 9(11):2505; Muhlestein, J. B. 2000, Curr. Interv.

Cardiol. Rep. 2(4):342. Another study supports this association when it was seen that elevated serum fibrinogen levels and total leucocyte count were found more often in those seropositive for *H. pylori*. Patel et al. 1995. B.M.J. 311:711.

A link between *Chlamydia pneumoniae* and vascular disease, such as atherosclerosis and coronary disease or coronary syndrome is also recognized. Schussheim et al., 1999, Drugs 57:283; Roivainen et al. 2000, Circulation 101(3):252; Muhlestein Curr. Interv. Cardiol. Rep. 2(4):342; Danesh et al. 1997, Lancet 350:430; Cheng et al. 2000, Expert Opin. Investig. Drugs 9(11):2505; Muhlestein, J. B. 2000, Curr. Interv. Cardiol. Rep. 2(4):342. Although *Chlamydia* is able to infect a number of cell types, the bacteria's ability to infect mononuclear phagocytes is thought to be pivotal to its role in the development or modulation of vascular disease, especially atherosclerosis. Mononuclear phagocytes are thought to spread infection from the respiratory tract to other organ systems based upon *Chlamydia* to remain metabolically active for at least 10 days in mononuclear phagocytes infected in vitro. Moazed et al. 1998. J. Infect Des. 177:1322. *Chlamydia* can also stimulate the secretion of proinflammatory cytokines such as tumor necrosis factor-·alpha·, interleukin [IL]-1 and interferon-·gamma· from monocytes and T cells. Saikku, P. 1997. J. Infect. Dis. 104:53; Kol et al. 1998. Circulation 98:300; Halne, S. 1997. Scand. J. Immunol. 45:378.

Several seroepidemiological studies now associate *Chlamydia* infection with atherosclerosis and promote the organism as a major pathological factor of this general disease process. Saikku, P. 1997. Scand. J. Infect. Dis. 104:53; Campbell et al. 1998. Emerg. Infect. Dis. 4:571. Recently, *C. pneumoniae*-reactive T lymphocytes have been detected in human atherosclerotic plaques of the carotid artery. Mosorin, M., 2000, Arterioscler. Thromb. Vasc. Biol. 20:1061. The authors of this study suggest that *Chlamydia*, which is commonly detected in atherosclerotic plaque of the carotid and coronary arteries, causes T-cell activation and accumulation and this contributes to the maintenance of the inflammatory reaction in artherogenesis.

At least one epidemiological study has found that *Chlamydia* may be present as an associated agent in neurological infections. See, Koskiniemi, M. et al., 1996, Europ. Neurol., 36(3):60-63. A human.

SUMMARY

In its most general aspect, the present invention provides a computer-implemented method of detecting at least one signal, which provides information which has diagnostic or prognostic significance.

In its most general embodiment, the method of the present invention includes acquiring image data of a sample of cells or a body fluid, processing the image data to select and record images of a detectable signal indicative of an infectious agent. Counts may be maintained of the number and/or strength of the detectable signal identified. The infectious agent may be contained within the image of an animal cell or free floating in the body fluid. Such counts provide for calculation of the extent of infection with an infectious agent(s).

In an embodiment, the image data is transformed from one color space, e.g., an RGB (Red Green Blue) image into another color space, e.g., HLS (Hue Luminescence Saturation) image. Filters and/or masks are utilized to distinguish those cells that meet pre-selected criteria, i.e. contain a detectable signal, and eliminate those that do not, and thus identify infected animal cells.

According to one embodiment, an infectious agent is detected or preferably detected and quantified by computer controlled image analysis of host cells, e.g., animal or plant cells. In a preferred embodiment, the host cells are animal cells in a sample of a body fluid or tissue from an animal. Using this preferred method, animal cells infected with an infectious agent are detected or preferably detected and quantified. In the discussion below, animal cells are discussed as an exemplary "host" cell. As would be understood by those skilled in the art, this is for discussion purposes only and the method would be understood to be useful, in context, for detection of an infectious agent in any "host", i.e., animal or plant cell.

According to this preferred embodiment of the method of the invention, computer controlled image analysis is conducted on a sample of body fluid or tissue containing animal cells in a monolayer treated to provide at least two different signals which can both be detected and quantified. At least two signals are required. A first signal is employed to identify an animal cell of interest and a second signal is employed to identify an infectious agent within an identified animal cell of interest. Detection and quantification of the two different signals provides for determination of: (1) the number of infected animal cells, e.g., per unit volume of body fluid, (2) the number of infectious agents per animal cell or (3) both the number of infected animal cells and the number of infectious agents per cell, i.e., the extent of cell infection.

According to the method, a monolayer of animal cells, fixed to a suitable solid substrate is observed by a computer controlled microscope system as described above. The monolayer can be obtained merely by spreading a body fluid or tissue sample with animal cells of interest on a solid substrate, such as a slide. Alternatively, a monolayer can be obtained by spreading a sample containing an enriched population of animal cells of interest on a solid substrate.

A physical feature of the animal cells can be used to provide a first signal, or more preferably the animal cells are stained to produce a first signal. The fixed animal cells are also treated to produce a second signal specific to an infectious agent, if said agent is present.

The computer controlled image analysis of this embodiment of the invention is accomplished using a computer software product including a computer-readable storage medium having fixed therein a sequence of instructions which, when executed by a computer directs the performance of method steps comprising:

A microscope image of an optical field of a substrate having fixed thereon a monolayer of animal cells treated to produce a first signal specific to a desired animal cell and a second signal specific to a desired infectious agent is acquired and transferred to the computer as an RGB image.

The Red component of the RGB image is transferred to a new monochrome grey-level image and clipped for pixel values of less than 50 to cut down signal noise.

The grey-level image is transformed to a binary image, a black and white image in which pixels with corresponding pixels in the Luminance image having grey-level values lower than the cut off point are set to a value indicative of the expected size of animal cells of interest (white).

An opening filter, successive applications of an erosion filter followed by a dilation filter, is applied for the removal of small noise particles from the binary image.

Application of a hole filling function fills the holes in the identified images.

The area of each image is measured and all images having an area of pixels equal to or greater than the expected value of the animal cell of interest are selected as representative of animal cells. Cell images that have an area less than said pixels are excluded from further processing.

The area, in pixels, of the cell images, i.e., animal cells, is recorded and saved for further processing. In one embodiment, in which all cell images are to be quantified in a sample, the XY location of each cell image is recorded.

The Red component from the original RGB image is transferred to a binary image, so that pixels having grey-level values less than the expected value of the signal indicative of an infectious agent are set to 0 while all the rest are set to 255.

The Green component from the original RGB image is transferred to grey level image.

All pixels that have a value equal to a set value M and any grey-level value in the Green component of the original RGB image equal to a set value N, together indicative of a particular signal form a new grey-level image.

This new grey-level image is transformed into a binary image where pixels that have grey-level values less than 100 are set to 0 and the rest of the pixels are set to.

An opening filter is applied to remove small noise particles from the binary image and a hole filling function is applied.

The total area of the remaining cell images, which represents the total area of infectious agent within the cell perimeter, is recorded.

Percent area of each animal cell that is occupied by an infectious agent can be calculated.

According to one mode of this embodiment of the invention, detection of infected animal cells can simply be recorded for each image or the process can be repeated for a number of optical fields and a number of images can be accessed up to an including the entire surface of a slide. Simple detection of infected animal cells provides useful information for diagnosis and/or prognosis as described in detail in Section 5.2, infra. In addition, the number of infected animal cells can be determined to provide even more useful information as described in Section 5.2, infra.

Alternatively, the percent area of an animal cell occupied by an infectious agent can be calculated. This provides quantitative information regarding extent of infection useful for diagnosis and/or prognosis as described in detail in Section 5.2, infra.

Additionally, according to an alternative of this mode of the embodiment of the invention, the number and positions of all animal cells on a slide can be determined.

According to another embodiment, an infectious agent is detected or preferably detected and quantified by computer controlled image analysis of a free floating infectious agent in a sample of a body fluid or tissue from an animal. In this embodiment, computer controlled image analysis is conducted on a sample of body fluid or tissue treated to provide at least one signal specific to the infectious agent of interest which can be detected and quantified.

The computer controlled image analysis of this embodiment of the invention is accomplished using a computer software product including a computer-readable storage medium having fixed therein a sequence of instructions which, when executed by a computer directs the performance of method steps comprising:

A microscope image of an optical field of a substrate having fixed thereon a sample of a body fluid or tissue treated to produce a signal specific to a desired infectious agent is acquired and transferred to the computer as an RGB image.

The image is transferred to the HLS domain.

The Hue component of the HLS image is transformed to a new monochrome greylevel image.

The greylevel image is transformed to a "binary" image: this is a black and white image in which pixels with pixels having values between 10 and 25 in the Hue image are set to 255 (white) and the rest being set to 0 black.

An "open" filter is applied: Opening is a successive application of an "erosion" filter followed by a "dilation" filter. It allows for the removal of small noise particles from the binary image and a hole filling function is applied that "fills the holes" in the identified blobs.

The area of the blobs is measured and all blobs that have an area of less than the expected area or size of the infectious agent are excluded from further processing. In an illustrative example, when the infectious agent is *Chlamydia*, all blobs that have an area of less than 30 pixels and more than 70 pixels are excluded from further processing. The remaining blobs represent infectious agent in the blood sample.

The pixel number (area) of these blobs (cells) is recorded and saved for further processing.

The information provided by the computer controlled image analysis methods of the present invention is useful, preferably in combination with other information relating to the physical and/or physiological state of a human or non-human patient in diagnosis of prognosis of a disease or disorder associated with infection of the human or non-human patient by an infectious agent. The information provided is useful for diagnosis or prognosis of diseases and disorders associated with a variety of infectious agents, including, but not limited to, prions, bacteria, mycoplasma, rickettsia, spirochetes, fungi, protozoal parasites, viruses, etc.

One particular embodiment of the present invention is a computer-implemented method for detecting a *Chlamydia* infected mononuclear phagocytes from a blood or tissue sample.

Another particular embodiment of the present invention is a computer-implemented method for detecting *Helicobacter pylori* infected mononuclear phagocytes from a blood or tissue sample.

Another particular embodiment of the present invention is a computer-implemented method for detecting CMV infected mononuclear phagocytes from a blood or tissue sample.

Another particular embodiment of the present invention is a computer-implemented method for detecting Herpes simplex virus infected mononuclear phagocytes from a blood or tissue sample.

Another particular embodiment of the present invention is a computer-implemented method for detecting mononuclear phagocytes infected with one or more of a variety of periodontal infectious agents such as *P. gingivalis, S. sanguis*, from a blood or tissue sample.

The present invention also encompasses a computer software product including a computer-readable storage medium having fixed therein a sequence of instructions which, when executed by a computer, direct the performance of steps for conducting the methods of the invention as described herein.

The present invention also encompasses to a method of operating a laboratory service for providing useful information for disease diagnosis and prognosis of disease extent or susceptibility or efficacy of a therapeutic treatment. The method encompasses the steps of receiving a prepared substrate, e.g. a slide, that has a monolayer of cells from a body fluid or tissue sample or receiving a body fluid or tissue sample where the body fluid or tissue sample is placed on a substrate as a monolayer, treating the sample to generate a diagnostic/prognostic signal, obtaining an image of a monolayer of cells, and operating a computerized microscope according to the method(s) described herein to provide the information useful to diagnose a disease or prognosticate disease susceptibility.

The present invention also provides a system for screening infected animal cells or infected body fluids or tissues. The basic elements of the system include an X-Y stage, a mercury light source, a fluorescence microscope, digital camera system such as a color CCD camera, or a complementary metal-oxide semiconductor (CMOS) image system, a personal computer (PC) system, and one or two monitors and most importantly a computer software product including a computer-readable storage medium having fixed therein a sequence of instructions which, when executed by a computer, direct the performance of steps for conducting the methods of the invention as described herein. In a preferred embodiment, the stage has an automated microscope feeder configured with it so that slides can be automatically moved into and out of position for image capture and/or analysis.

3.1. OBJECTS AND ADVANTAGES OF THE INVENTION

It is an object of the invention to provide methods and systems which provide quantitative information regarding animal (human or non-human) cells infected with an infectious agent. Unlike other methods which provide merely for the detection of an infectious agent, the present methods and systems advantageously provide quantitative information with respect to infectious agents present in animal cells. Such information, preferably, in combination with other information relating to the physical and/or physiological state of a human or non-human patient, is useful in diagnosis or prognosis of a disease or disorder associated with the presence infectious agent. Unlike other methods which merely detect the presence of an infectious agent, in certain embodiments the methods and systems of the present invention can provide detailed information relating to the life cycle state and form of an infectious agent.

It is another object of the invention to provide methods and systems which provide quantitative information regarding the presence of an infectious agent "free floating" in an animal human or non-human) body fluid or tissue sample. Such quantitative information, preferably in combination with other family/genetic heritage, genetic profile, physical and/or physiological information relating to the heredity, physical and/or physiological state of a human or non-human patient, is useful in prediction of susceptibility, diagnosis or prognosis of a disease or disorder associated with the presence of the infectious agent.

In certain embodiments, the quantitative information provided by the methods of the invention is used to assess therapeutic efficacy of a treatment which the human or non-human patient is undergoing.

In certain other embodiments, the quantitative information provided by the methods of the invention is used to assess susceptibility of the human or non-human animal to recurrence or progress of a recurring or progressive disease or disorder.

In certain other embodiments, the quantitative information provided by the methods of the invention, along with information regarding the family history and/or genetic profile of relevant genes of a patient is used to predict chance of onset of a disease, advantageously prior to onset of clinical symptoms. In certain modes of these embodiments, the information is included in a "wellness" check or profile of the patient. For one example, application of the methods of the invention to monitor patient samples "over" time can be used to assess a patient's ability to clear a bacterial infection from monocytes and hence assess susceptibility to developing vascular disease.

BRIEF DESCRIPTION OF THE DRAWINGS

The present invention may be understood more fully by reference to the following detailed description of the invention, illustrative examples of specific embodiments of the invention and the appended figures in which:

In FIG. 2, the infectious agent is exemplified by *Chlamydia*; however, as would be understood by those skilled in the art, any of the infectious agents taught in this application could be detected and quantified according to the method illustrated in FIG. 2.

DETAILED DESCRIPTION OF INVENTION

The invention will be better understood upon reading the following detailed description of the invention and of various exemplary embodiments of the invention, in connection with the accompanying drawings. It will be clear to those skilled in the art that the invention can be applied to and, in fact, encompasses methods and systems to provide information useful in making a disease diagnosis or a prognosis of disease or disease susceptibility or outcome based on detection and preferably, quantification of any characteristic resulting from infection of a host, e.g., an animal cell with an infectious agent. The animal cell can be obtained from any fluid or tissue sample from which it is possible to view a monolayer of cells infected with said infectious agent. It will also be clear to those skilled in the art that the invention can be applied to, and in fact, encompasses methods and systems to provide information useful in making a disease diagnosis or prognosis of disease or disease susceptibility or outcome based on detection, and preferably quantification, of any characteristic indicative of the presence of an infectious agent "free floating" in a body fluid or tissue sample.

For the purpose of this invention, information useful for disease diagnosing or prognosis, evaluation of patient wellness or prediction of disease onset is based upon detection of a signal associated with a characteristic resulting from an infection of a animal cell, tissue or body fluid. The term "characteristic" as used herein is defined to mean any non-endogenous substance(s) that indicates the presence of an infectious agent in a animal cell, issue or body fluid, e.g. DNA, RNA, protein, carbohydrate, endotoxin, etc. indicative of or specific to an infectious agent. Fluid and tissue samples that can be used in the methods of the invention include but are not limited to blood or a "fraction" thereof such as white blood cells or a specific category of white blood cells, etc., tissue biopsies, spinal fluid, meningeal fluid, urine, alveolar fluid, etc.

In one aspect, the invention is described in connection with observing a "monolayer" of cells. Monolayer has a specific meaning as used herein. It means simply that the cells are arranged whereby they are not viewed on top of one another. It does not require confluence and can involve single cell suspensions. Thus, a monolayer can be viewed in smears of single cell suspensions or a layer of tissue that has a thickness of a single cell. Any solid or exfoliative cytology technique may also be employed. Cells may be dissociated by standard techniques known to those skilled in the art. These techniques include but are not limited to trypsin, collagenase or dispase treatment of the tissue.

In another aspect, the invention is described in connection with observing a "free floating" infectious agent. Free floating has a specific meaning as used herein. It means simply that the infectious agent present in a body fluid or tissue is not contained within the confines of an animal cell. It does not require that the infectious agent "float" in a biological fluid or tissue and the infectious agent can be attached e.g., to the periphery of a cell or tissue. It simply is not inside an animal cell.

According to a preferred embodiment of the invention, the animal cells are mononuclear phagocytes. As used herein, the term "mononuclear phagocytes" is intended to comprise, without limitation, monocytes obtained from a central or peripheral blood, macrophages obtained from any site, including any tissue or cavity, macrophages derived by incubating or culturing macrophage precursors obtained from bone marrow or blood. According to a more preferred embodiment, the mononuclear phagocytes are obtained from peripheral blood samples.

For the purpose of this invention, an "infectious agent" is intended to mean an organism or other agent, capable of replication and associated with a disease or disorder when said agent infects a host, such as an animal host or a plant host. Infectious agents include, but are not limited to, prions, bacteria, mycoplasma, rickettsia, spirochetes, fungi, parasites, protozoa, viruses, etc.

In an important embodiment, the infectious agent is a *Chlamydia* species. Common *Chlamydia* include: *C. pneumoniae, C. trachomatis, C. psittaci* and *C. pecorum*.

In another important embodiment, the infectious agent is a *Helicobacter* species. Common *Helicobacter* include: *H. pylori* and *H. felis*.

In another important embodiment, the infectious agent is a *Borrelia* species. Common *Borrelia* include: *B. burgdorferi* and *B. recurrentis*.

In another important embodiment, the infectious agent is a common periodontal bacteria. Common periodontal bacteria include: *P. gingivalis*, and *P. sanguis*.

In yet another important embodiment, the infectious agent is a Herpes virus, such as Herpes simplex virus or Cytomegalovirus.

Solely for ease of explanation, the description of the invention is divided into the following sections: (1) methods and systems (including apparatus) for detection and quantification of an infectious agent, including quantification of an infectious agent (a) in an animal cell and (b) "free floating" in a body fluid or tissue sample; and (2) applications and diseases and disorders for which useful information is provided.

5.1. Methods and Systems for Detection or Detection and Quantification

The present invention provides methods, apparatus and systems for the rapid detection and, more preferably, detection and quantification of an infectious agent in a biological sample. The methods employ apparatus and systems which afford computer controlled automated image analysis.

Figure 1:
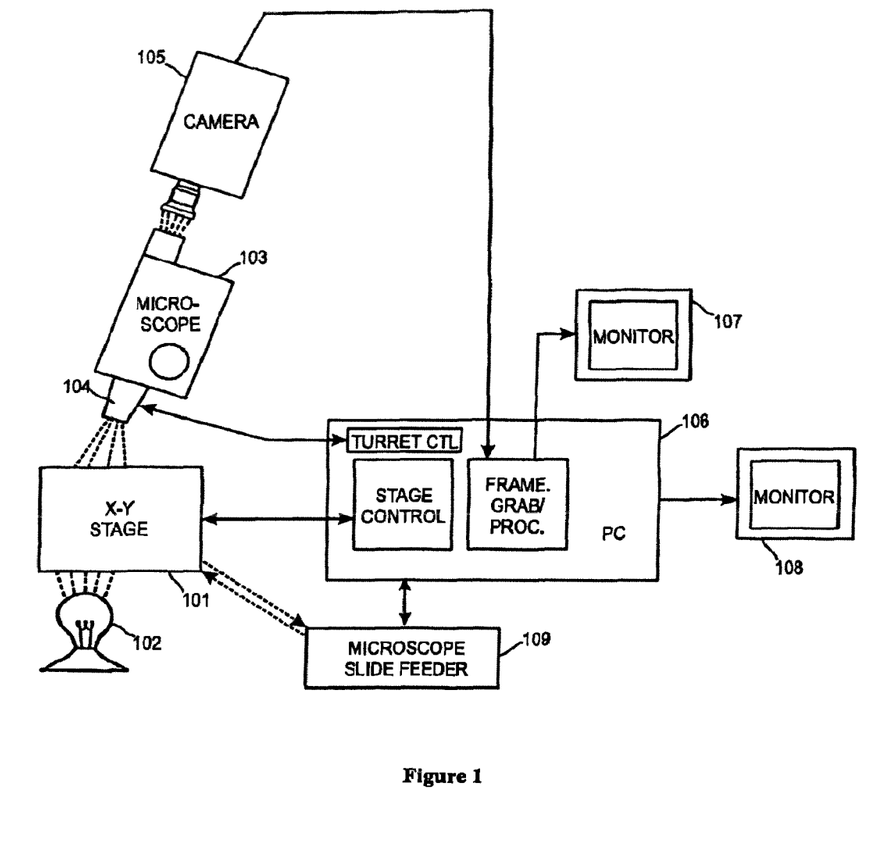
FIG. 1 is schematic representation of an apparatus or system useful for the methods of the invention. The automated microscope slide feeder (109) depicted in FIG. 1 is an optional component of a preferred system useful for the methods of the invention.

FIG. 1 illustrates the basic elements of a system suitable for use according to the methods of the invention. A system such as illustrated in FIG. 1 can be used in any of the methods described in the sub-sections below. The basic elements of the system include an X-Y stage (101), a mercury light source (102), a fluorescence microscope (103), a color CCD camera or CMOS image sensor (105), a personal computer (PC) system (106), and one or two monitors (107 and 108). In a preferred embodiment, the stage has an automated microscope feeder (109) configured with it so that slides can be automatically moved into and out of position for image capture and/or analysis.

The individual elements of the system can be custom built or purchased off-the-shelf as standard components. Each element is described in somewhat greater detail below.

The X-Y stage can be any motorized positional stage suitable for use with the selected microscope. Preferably, the X-Y stage can be a motorized stage that can be connected to a personal computer and electronically controlled using specifically compiled software commands. When using such an electronically controlled X-Y stage, a stage controller circuit card plugged into an expansion bus of the PC connects the stage to the PC. The stage should also be capable of being driven manually. Electronically controlled stages such as described here are produced by microscope manufacturers, for example including Olympus (Tokyo, Japan), as well as other manufacturers, such as LUDL (NY, USA).

The microscope can be any fluorescence microscope equipped with a reflected light fluorescence illuminator and a motorized objective lens turret with a 20·times·, 40·times·, and 100·times· (with or without oil immersion) objective lens, providing a maximum magnification of 1000·times·. The motorized nosepiece is preferably connected to the PC and electronically switched between successive magnifications using specifically compiled software commands. When using such an electronically controlled motorized nosepiece, a nosepiece controller circuit card plugged into an expansion bus of the PC connects the stage to the PC. The microscope and stage are set up to include a mercury light source, capable of providing consistent and substantially even illumination of the complete optical field.

The microscope produces an image viewed by the camera. The camera can be any color 3-chip CCD camera or other camera or digital image sensor system connected to provide an electronic output and providing high sensitivity and resolution. The output of the camera is fed to a frame grabber and image processor circuit board installed in the PC. A camera found to be suitable is the OPTRONICS 750 (OPTRONICS, CA.). Another digital camera found to be suitable is the complementary metal-oxide semiconductor system (CMOS) image sensor available from Photobit (Pasadena, Calif.).

Various frame grabber systems can be used in connection with the present invention. The frame grabber can be, for example, the MATROX GENESIS available from MATROX (Montreal, CANADA). The MATROX GENESIS module features on-board hardware supported image processing capabilities. These capabilities compliment the capabilities of the MATROX IMAGING LIBRARY (MIL) software package. Thus, it provides extremely fast execution of the MIL based software algorithms. The MATROX boards support display to a dedicated SVGA monitor. The dedicated monitor is provided in addition to the monitor usually used with the PC system. Any monitor SVGA monitor suitable for use with the MATROX image processing boards can be used. One dedicated monitor usable in connection with the invention is a ViewSonic 4E (Walnut Creek, Calif.) SVGA monitor.

In order to have sufficient processing and storage capabilities available, the PC can be any PC such as an INTEL PENTIUM-based PC having at least 256 MB RAM and at least 40 GB of hard disk drive storage space. The PC preferably further includes a monitor. Other than the specific features described herein, the PC is conventional, and can include keyboard, printer or other desired peripheral devices not shown.

Alternatively, automated sample analysis may be performed by an apparatus and system for distinguishing, in an optical field, objects of interest from other objects and background, such as the automated system exemplified in U.S. Pat. No. 5,352,613, issued Oct. 4, 1994 (incorporated herein by reference). Furthermore, once an object, i.e., a relevant animal cell has been identified, the color, e.g. the combination of the red, green, blue components for the pixels that comprise the object, or other parameters of interest relative to that object, i.e., whether it is infected or not by an infectious agent, can be measured and stored.

Other examples of alternative apparatus and systems for automated sample analysis are illustrated in WO99/58972 and PCT/US00/31494 (incorporated herein by reference).

One suitable system consists of an automatic microscopical sample inspection system having:

a sample storage module and loading and unloading module a sample transporting mechanism to and from an automated stage that moves the sample under a microscope objective lenses array an array of CCD cameras a processing unit having a host computer, multiple controllers to control all mechanical parts of the microscopy system and a high speed image processing unit where the CCD cameras are connected (see, PCT/US00/31494).

An innovative feature of this embodiment of a computer controlled system is an array of two or more objective lenses having the same optical characteristics. The lenses are arranged in a row and each of them has its own z-axis movement mechanism, so that they can be individually focused. This system can be equipped with a suitable mechanism so that the multiple objective holder can be exchanged to suit the same variety of magnification needs that a common single-lens microscope can cover. Usually the magnification range of light microscope objectives extends from 1·times· to 100·times.

Each objective is connected to its own CCD camera. The camera field of view characteristics are such that it acquires the full area of the optical field as provided by the lens.

Each camera is connected to an image acquisition device. This is installed in a host computer. For each optical field acquired, the computer is recording its physical location on the microscopical sample. This is achieved through the use of a computer controlled x-y mechanical stage. The image provided by the camera is digitized and stored in the host computer memory. With the current system, each objective lens can simultaneously provide an image to the computer, each of which comprises a certain portion of the sample area. The lenses should be appropriately corrected for chromatic aberrations so that the image has stable qualitative characteristics all along its area.

The imaged areas will be in varying physical distance from each other. This distance is a function of the distance at which the lenses are arranged and depends on the physical dimensions of the lenses. It will also depend on the lenses' characteristics, namely numerical aperture and magnification specifications, which affect the area of the optical field that can be acquired. Therefore, for lenses of varying magnification/numerical aperture, the physical location of the acquired image will also vary.

The computer will keep track of the features of the objectives-array in use as well as the position of the motorized stage. The stored characteristics of each image can be used in fitting the image in its correct position in a virtual patchwork, e.g. "composed" image, in the computer memory.

The host computer system that is controlling the above configuration, is driven by software system that controls all mechanical components of the system through suitable device drivers. The software also comprises properly designed image composition algorithms that compose the digitized image in the computer memory and supply the composed image for processing to further algorithms. Through image decomposition, synthesis and image processing specific features particular to the specific sample are detected.

5.1.1. Methods for Detection or Detection and Quantification of Agent Inside an Animal Cell According to one embodiment, an infectious agent is detected or preferably detected and quantified by computer controlled image analysis of animal cells in a sample of a body fluid or tissue from an animal. Using this method, animal cells infected with an infectious agent are detected or preferably detected and quantified.

According to this embodiment of the method of the invention, computer controlled image analysis is conducted on a sample of body fluid or tissue containing animal cells in a monolayer treated to provide at least two different signals which can both be detected and quantified. At least two signals are required. A first signal is employed to identify an animal cell of interest and a second signal is employed to identify an infectious agent within an identified animal cell of interest. Detection and quantification of the two different signals provides for determination of: (1) the number of infected animal cells, e.g., per unit volume of body fluid, (2) the number of infectious agents per animal cell or (3) both the number of infected animal cells and the number of infectious agents per cell, i.e., the extent of cell infection.

As used herein, "signal" should be taken in its broadest sense, as a physical manifestation which can be detected and identified, thus carrying information. One simple and useful signal is the light emitted by a fluorescent dye selectively bound to a structure of interest. That signal indicates the presence of the structure, i.e., either an animal cell or an infectious agent, which might be difficult to detect absent the fluorescent dye.

The requirements and constraints on the generation of the first signal and second signal are relatively simple. The materials and techniques used to generate the first signal should not interfere adversely with the materials and techniques used to generate the second signal (to an extent which compromises unacceptably detection and quantification), and visa versa. Nor should they damage or alter the cell- or infectious agent-specific characteristics sought to be measured to an extent that compromises unacceptably the detection and quantification. Finally, any other desirable or required treatment of the cells should also not interfere with the materials or techniques used to generate the first signal and second signal to an extent that compromises unacceptably the detection and quantification. Within those limits, any suitable generators of the first signal and second signal may be used.

According to the method, a monolayer of animal cells, fixed to a suitable solid substrate is observed by a computer controlled microscope system as described above. The monolayer can be obtained merely by spreading a body fluid or tissue sample with animal cells of interest on a solid substrate, such as a slide. Alternatively, a monolayer can be obtained by spreading a sample containing an enriched population of animal cells of interest on a solid substrate. Enrichment of animal cells of interest can be accomplished by any means known to those skilled in the art, such as centrifugation, affinity purification, etc. A physical feature of the animal cells can be used to provide a first signal, or more preferably the animal cells are stained to produce a first signal. The fixed animal cells are also treated to produce a second signal specific to an infectious agent, if said agent is present. Optionally, the method is conducted using animal cells already fixed on a substrate, e.g. a slide. Alternatively, as part of the method of the present invention, the cells may be prepared on a substrate before being treated. Preparing the cells may be accomplished by first obtaining a sample, washing the cells, and fixing the cells on a substrate. It should be evident that any means of obtaining, collecting, washing, and fixing the cells may be used depending on the infected animal cell to be detected.

The body fluid or tissue sample may be obtained by a number of ways depending upon where the infected cell resides. If, for example, the infected cell resides in blood, a minimally invasive procedure, such as taking a blood sample, may be all that is necessary to obtain the cells. As an illustrative example, *Chlamydia* infected mononuclear phagocytes can be observed and quantitated in a peripheral blood sample. A similar minimally invasive procedure may be used if the infected cell resides in a mucosa layer. In an alternative embodiment of the present invention, a sample may be taken by a more invasive procedure if desired. For example, a biopsy may be performed in order to obtain a sample to identify an infected animal cell needed to make a diagnosis or prognosis with the present invention.

Treating the cells may occur with a fluorescent dye bound to an antibody against the characteristic that specifically identifies the infectious agent. The animal cells may be simply counterstained with an agent that fluoresces at a wavelength different from that of the fluorescent dye bound to the antibody specific for the infectious agent. Alternatively, animal cells are treated with a fluorescent dye bound to an antibody specific for the animal cells which dye fluoresces at a wavelength different from that of the dye bound to the antibody specific for the infectious agent. It should now be evident that any two detectable indicators of the presence of an infected animal cell may serve as the first and second signals, subject to certain constraints noted herein.

As would be understood by those skilled in the art, for each infectious agent to be detected, specific reagents are required to generate the signals needed to detect the infected animal cell. For example, for the embodiment in which *Chlamydia* infected mononuclear phagocytes are detected, a labelled antibody directed to *Chlamydia* can be used in generating the signal. Three examples of commercially available antibodies are: (1) ChlamydiaCel, a genus-specific lipopolysaccharide monoclonal antibody that identifies *C. pneumoniae*, as well as *C. trachomatis* and *C. psittaci*, with a strong fluorescence of the intracellular inclusions, the pinhead-sized elementary bodies and the free cell-associated *Chlamydia* LPS antigens (CelLabs, Sydney, Australia), (2) *Chlamydia* CelPn, a *C. pneumoniae* specific monoclonal antibody (CelLabs, Sydney, Australia), and (3) a *Chlamydia* specific FITC-conjugated monoclonal antibody (Kallestad Diagnostics, Chaska, Minn.). Other illustrative examples of commercially available antibodies specific to cells of interest or infectious agents of interest that are useful in the methods and systems of the invention include: Clone MCA38, mouse monoclonal antibody to human monocytes/macrophages (Research Diagnostics Inc., Flanders, N.J.); Clone B2, monoclonal antibody for the detection of cytomegalovirus (Research Diagnostics Inc., Flanders, N.J.); Clone A33, monoclonal antibody for the detection of herpes simplex virus (Research Diagnostics Inc., Flanders, N.J.); Antibody 05-97-92, affinity purified antibody to *Borrelia* species (Kirkegaard and Perry Laboratories, Gaithersburg, Md.); and Monoclonal antibody A94000136P, to *Helicobacter pylori*, (BiosPacific, Emeryville, Calif.).

As would be understood by those skilled in the art, antibodies or antibody fragments specific for any host cell of interest or any infectious agent can be produced by any method known in the art for the synthesis of antibodies (or binding fragments thereof, in particular, by chemical synthesis or preferably, by recombinant expression techniques.

Polyclonal antibodies to a host cell of interest or in infectious agent of interest can be produced by various procedures well known in the art. For example, a host cell of interest, an infectious agent or antigen thereof can be administered to various host animals including, but not limited to, rabbits, mice, rats, etc. to induce the production of sera containing polyclonal antibodies specific for the infectious agent or host cell or antigen thereof. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a host cell of interest or antigenic part thereof, infectious agent or antigen thereof and once an immune response is detected, e.g., antibodies specific for the host cell of interest or infectious agent are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding an infectious agent or host cell of interest. Ascites fluid, which generally contains high levels of antibodies, can be generated by immunizing mice with positive hybridoma clones.

Antibody fragments which recognize specific epitopes of a host cell or of an infectious agent may be generated by any technique known to those of skill in the art. For example, Fab and F(ab')2 fragments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain. Further, the antibodies useful to generate a signal (e.g., when labelled) can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to a host cell or an infectious agent of interest can be selected or identified with a host cell infectious agent or antigen thereof, e.g., using labeled antigen or antigen bound or captured to a solid surface or bead. Examples of phage display methods that can be used to make the antibodies useful in the method of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT application No. PCT/GB91/O1 134; PCT publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1·alpha· promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

Alternatively, the second signal, which indicates the presence of a particular characteristic of an infectious agent being tested for, and may be generated, for example, using technologies in which nucleic acids specific to the infectious agent are labelled and detected using techniques including such as in situ PCR-amplification or PCR in situ hybridization or FISH.

Cells that emit both signals, e.g. the cell is an infected animal cell and contains the characteristic being tested for with the second signal, are scored. Counts may be maintained of the number and strengths of the first signal and second signal detected.

While the description herein explains the method with respect to mononuclear phagocytes (or monocytes) as the host, e.g., animal cells; blood as the body fluid or tissue sample and Chlamydia as the infectious agent, it would be understood by those skilled in the art that the invention can be applied to and in fact, encompasses computer controlled automated image analysis of any type of host cell and any body fluid or tissue sample infected by any relevant infectious agent. Hence, it is understood that the following description is merely explained, for purposes of ease of explanation and is illustrated in FIGS. 2 and 3, with respect to detection and quantification of mononuclear phagocytes infected with Chlamydia.

Figure 2:
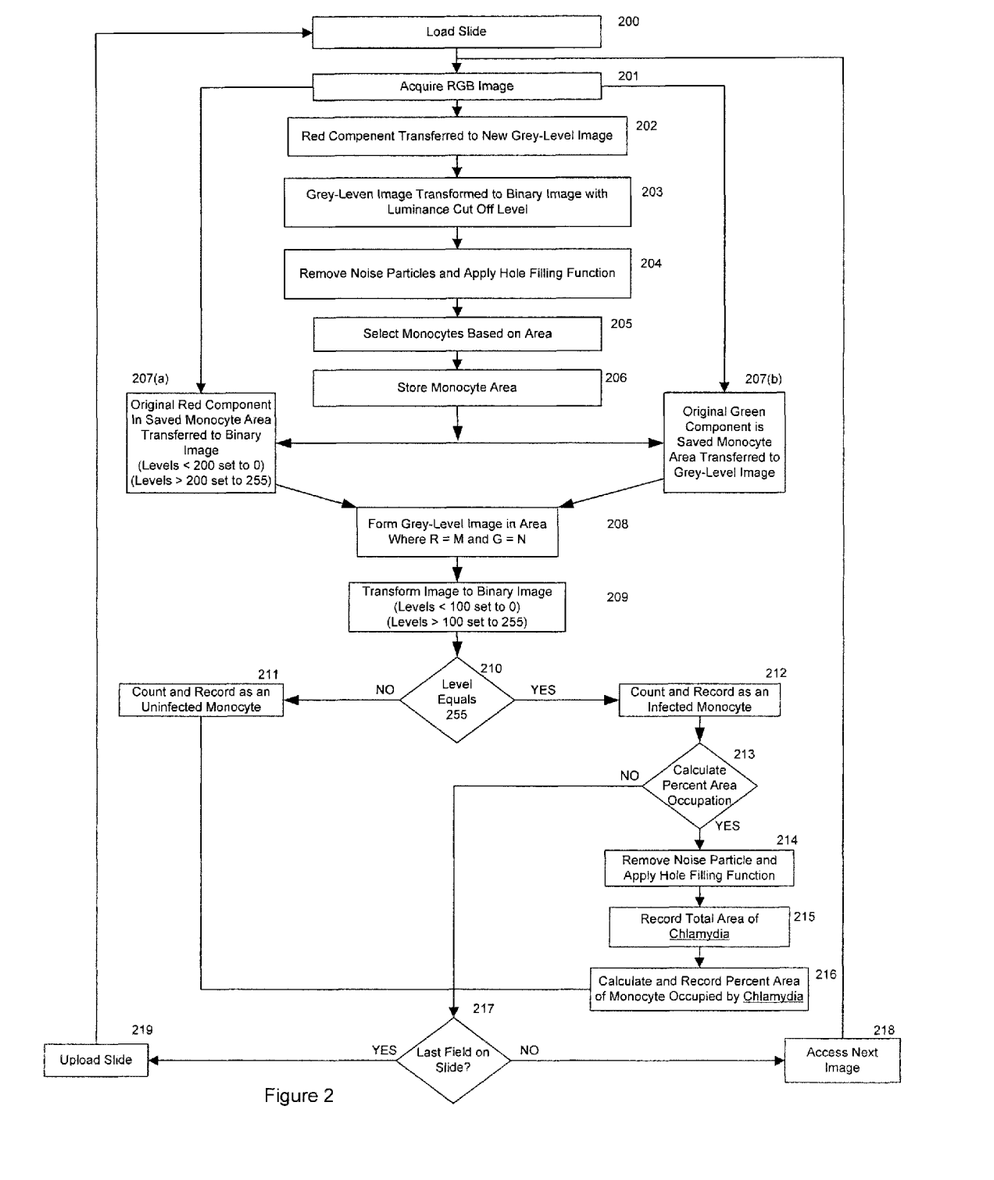
FIG. 2 is a flow chart summarizing the method of one aspect of the invention in which an infectious agent is detected or detected and quantified in an animal cell.
Figure 3:
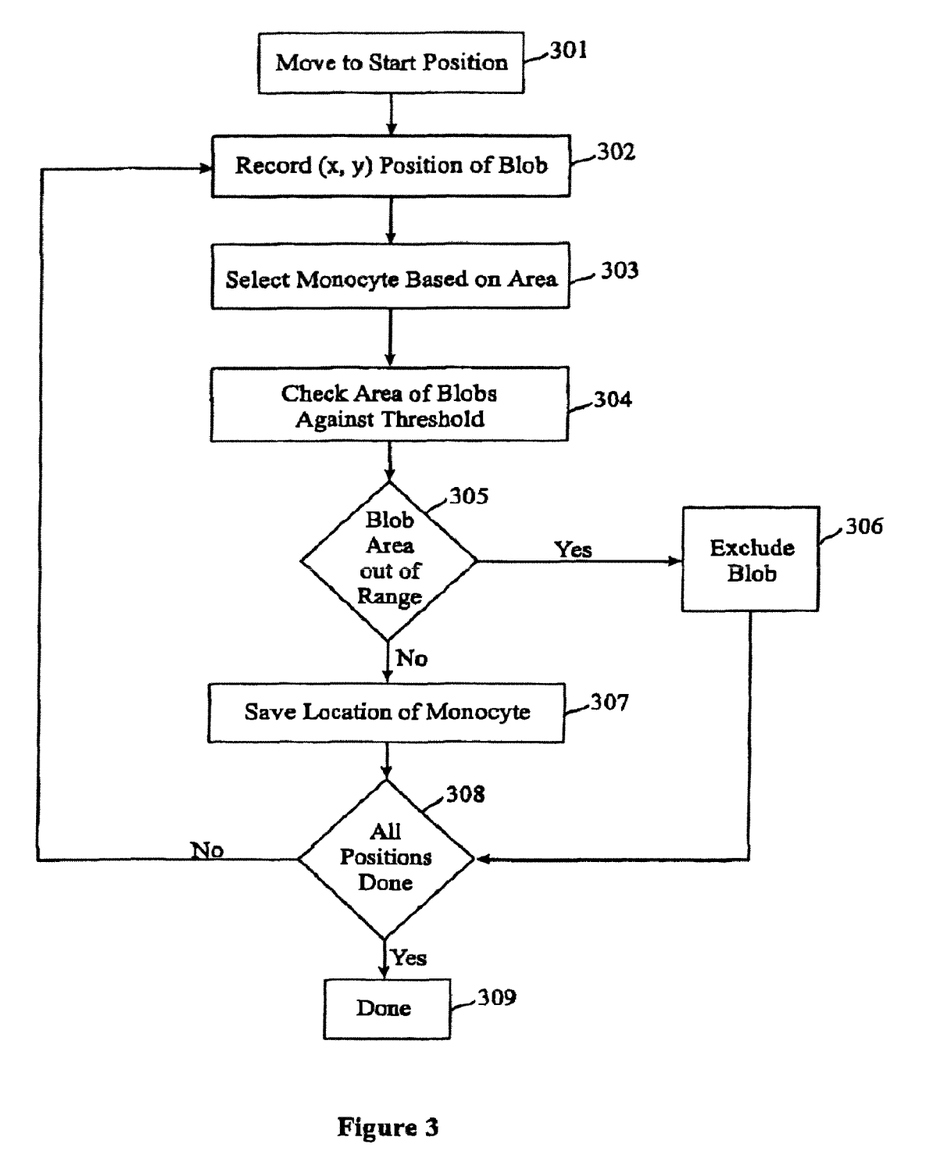
FIG. 3 is a more detailed flow chart of portions of an alternative embodiment of the method of the aspect of the invention shown in FIG. 2.

FIG. 2 schematically illustrates one embodiment of one method of the invention, using monocytes as the animal cells and Chlamydia as the infectious agent, merely for ease of explanation.

An objective, e.g., the 100·times· objective is selected to provide total magnification of 1000·times· and a slide containing a monolayer of treated animal cells (from an animal suspected of infection with Chlamydia) is placed on the automated stage.

As illustrated in FIG. 2, a slide is loaded (200), (preferably using an automated slide loader.

The program moves the automated stage to a preset starting point, e.g., on a corner of the slide.

Optionally, the x-y position of the stage at the starting point is recorded.

An optical field is selected and the microscopic image is acquired and transferred to the computer as an RGB image (201).

The Red component of the RGB image is transferred to a new monochrome grey-level image and clipped for pixel values of less than 50 to cut down signal noise (202).

The grey-level image is transformed to a binary image, a black and white image in which pixels with corresponding pixels in the Luminance image having grey-level values lower than the cut off point are set to 255 (white) (203).

Noise particles are removed and a hole filling function is applied to the binary image (204). In an illustrative embodiment, (see infra Section 6) a commercially available MATROX function is used to fill the holes in the identified images. The area of each image is measured and all, images having an area of expected for a monocyte or mononuclear phagocyte, i.e., 1000 pixels or greater are selected as representative of mononuclear phagocytes. Cell images that have an area less than 1000 pixels are excluded from further processing (205).

The area, in pixels, of the cell images, i.e., mononuclear phagocytes, is recorded and saved for further processing (206). Optionally, the XY location of mononuclear phagocytes is recorded for later analysis and/or processing.

The original Red component from the original RGB image is transferred to a binary image, so that pixels having grey-level values less than 200 are set to 0 while all the rest are set to 255 (207a).

The original Green component is transferred to grey level image (207b).

All pixels that have a value of M and any grey-level value in the Green component of the original RGB image equal to N form a new grey-level image (208). In a specific illustrative embodiment exemplified infra in Section 6 when a first signal indicative of a monocyte is generated using counter stain with 4'-6-Diamidino-2-phenylindole is detected and a second signal indicative of *Chlamydia* is detected using fluorophore conjugated ChlamydiaCel monoclonal antibody available from (CelLabs, Sydney, Australia) is used, M is set at 255 and N is set at 0.

This new grey-level image is transformed into a binary image where pixels that have grey-level values less than 100 are set 0 and the rest of the pixels are set to 255 (209).

If the level is 255, the monocyte is counted and recorded as an *Chlamydia*-infected monocyte (212); if not, the monocyte is recorded as not infected (211).

The extent of infection of individual *Chlamydia* infected monocytes can be determined:

An opening filter is applied to remove small noise particles from the binary image and a hole filling function is applied (214)

The total area of the remaining cell images, which represents the total area of *Chlamydia* organisms within the cell perimeter is recorded (215)

Percent area of each mononuclear phagocyte that is occupied by *Chlamydia* organisms can be calculated (216).

As illustrated in FIG. 2, according to one mode of this embodiment of the invention, detection of *Chlamydia* infected monocytes can simply be recorded for each image (210-212) or the process can be repeated for a number of optical fields and a number of images can be accessed (218) up to an including the entire surface of a slide (218-217). Simple detection of infected monocytes provides useful information for diagnosis and/or prognosis as described in detail in Section 5.2, infra. In addition, the number of infected monocytes can be determined to provide even more useful information as described in Section 5.2, infra.

Alternatively, as further illustrated in FIG. 2, the percent area of a monocyte occupied by *Chlamydia* is calculated (213-216). This provides quantitative information regarding extent of infection useful for diagnosis and/or prognosis as described in detail in Section 5.2, infra.

FIG. 3 schematically illustrates an alternative mode of this embodiment of the invention. As illustrated in FIG. 3, according to an alternative of this mode of the embodiment of the invention, the number and positions of all monocytes on a slide are determined. In this mode of this embodiment of the present invention, *Chlamydia* infection of monocytes can be detected or detected and quantified using the steps illustrated in FIG. 2 either after recordation of each monocyte image (see FIG. 3, 307) or after all monocyte images have been recorded (see FIG. 3, 309). This provides information useful as described in Section 5.2, infra.

As would be understood by those skilled in the art, the parameters to set levels of image detection for animal cells and for infectious agents will depend upon the specific animal cells and infectious agents to be detected as well as upon the specific first and second signals used to detect the cells and infectious agents. Such parameters can be determined by those skilled in the art using known methods and the information provided herein.

5.1.2. Methods for Detection or Detection and Quantification of a Free-Floating Agent According to another embodiment, an infectious agent is detected or preferably detected and quantified by computer controlled image analysis of a free floating infectious agent in a sample of a body fluid or tissue from an animal. In this embodiment, computer controlled image analysis is conducted on a sample of body fluid or tissue treated to provide at least one signal specific to the infectious agent of interest which can be detected and quantified. As would be understood by those skilled in the art, the same signals specific for an infectious agent described in Section 5.1.1., supra, are suitable for use in this embodiment of the invention.

A slide containing, for example, a blood smear from a patient suspected of infection with *Chlamydia* is properly immunostained, for example, using the following steps: blood smears are washed with phosphate-buffered saline, fixed with methanol and stained directly with *Chlamydia* genus-specific FITC-conjugated monoclonal antibody obtained e.g. from (Kallestad Diagnostics, Chaska, Minn.).

Images are captured at 1000·times· total magnification. The PC (see FIG. 1, 106) software program compiled in MICROSOFT C++ using the MATROX IMAGING LIBRARY (MIL). MIL is designed by MATROX to control the operation of the frame grabber and the processing of images captured by frame grabber and subsequently stored in PC as disk files. It comprises a number of image processing specialized routines particularly suitable for performing such image processing task as filtering, object selection and various measurement functions. The program prompts and measurement results are shown on the computer monitor (see FIG. 1, 108).

Figure 4:
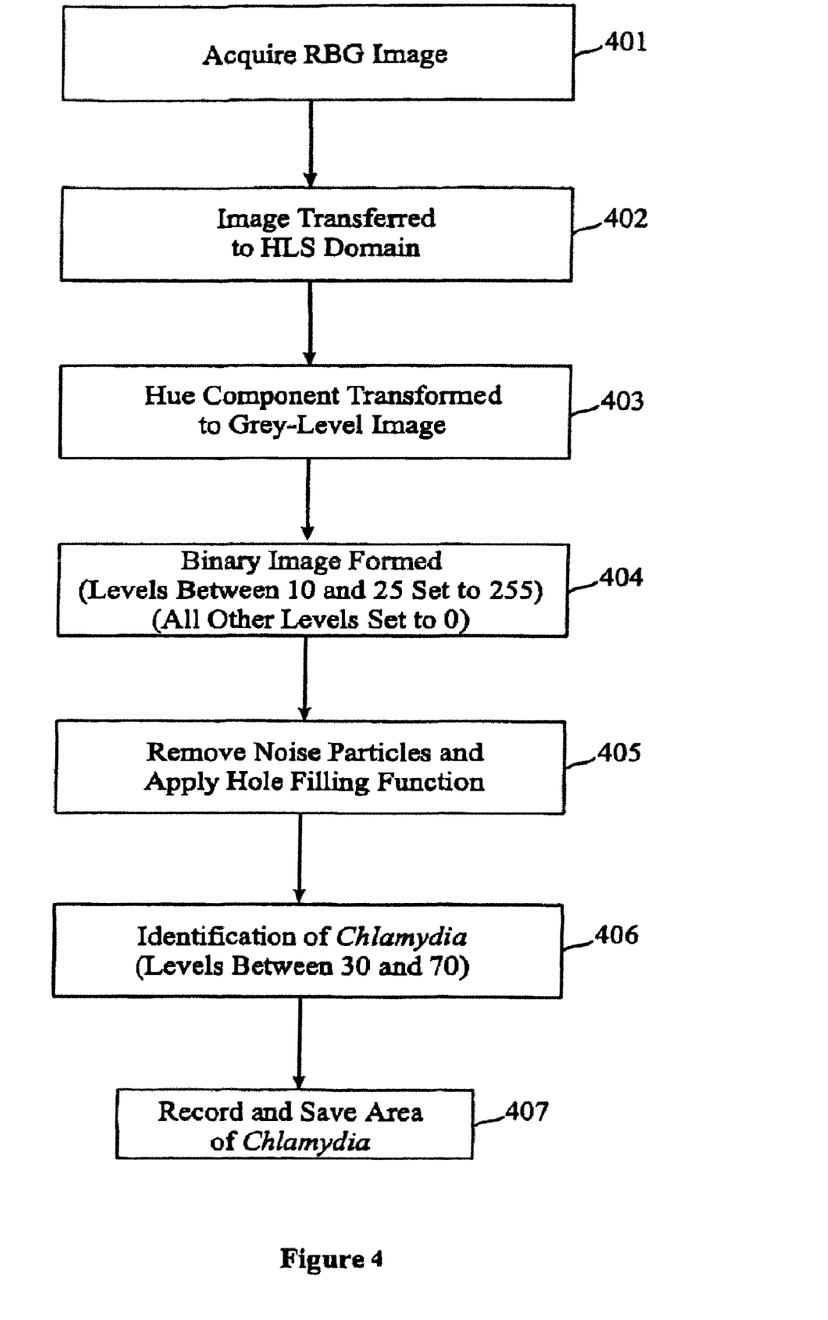
FIG. 4 is a flow chart summarizing the method of another aspect of the invention in which an infectious agent is detected or detected and quantified "free floating" in a biological sample from an animal.

FIG. 4 schematically illustrates this embodiment of the method of the invention, using *Chlamydia* as the infectious agent, merely for illustrative purposes and ease of explanation.

As illustrated in FIG. 4, detection or detection and quantification of free floating *Chlamydia* in a blood sample on a microscope slide is achieved as follows:

An optical field is selected and the microscopic image is acquired and transferred to the computer as an RGB image (401);

The image is transferred in the HLS domain (402);

The Hue component of the HLS image is transformed to a new monochrome grey-level image (403);

A "binary" image is formed: this is a black and white image in which pixels with pixels having values between 10 and 25 in the Hue image set to 255 (white) and the rest being set to 0 black (404);

An "open" filter is applied: Opening is a successive application of an "erosion" filter followed by a "dilation" filter. It allows for the removal of small noise particles from the binary image. A hole filling function is applied. (405);

The area of the blobs is measured and all blobs that have an area of less than 30 pixels and more than 70 are excluded from further processing. The remaining blobs represent identified *Chlamydia* particles in the blood sample (406);

The pixel number (area) of these blobs (cells) is recorded and saved for further processing (407).

5.2. Diseases, Disorders and Applications

The information provided by the computer controlled image analysis methods of the present invention is useful, preferably in combination with other information relating to the genetic/hereditary, physical and/or physiological state of a human or non-human patient, in diagnosis or prognosis of a disease or disorder associated with infection of the human or non-human patient by an infectious agent. Prognosis encompasses determination of the susceptibility to disease onset or progression, spread or recurrence, of extent of disease or of whether a treatment a patient is undergoing is effective in ameliorating, preventing or curing a disease or disorder from which the patient is suffering. The information provided is useful for diagnosis or prognosis of diseases and disorders associated with a variety of infectious agents, including, but not limited to, prions, bacteria, mycoplasma, rickettsia, spirochetes, fungi, protozoal parasites, viruses, etc.

In certain embodiments, the methods provide information useful and sufficient to diagnose a disease or disorder caused by an infectious agent. As an illustrative example, the methods of the invention are used to detect or detect and quantitate the presence of *Chlamydia pneumoniae* in a body fluid or tissue sample to diagnose the presence of pneumonia caused by said infectious agent. As another illustrative example, the methods of the invention are used to detect and quantitate the presence of *Borrelia* in a body fluid or tissue sample to diagnose the presence of Lyme disease caused by said infectious agent.

Thus, in certain embodiments, simple detection of the presence of an infectious agent either in an animal cell or free floating in a body fluid or tissue provides sufficient information to diagnose a disease caused by the infectious agent. In other embodiments, quantitative information regarding the extent or presence of an infectious agent, e.g. a virus is useful for prognosis of a disease cause by the infectious agent.

In yet other embodiments, the quantitative information regarding an infectious agent provided by the methods of the invention is used to determine therapeutic efficacy of a treatment which a patient infected with an infectious agent is undergoing.

In an important specific embodiment, the invention provides is a unique method to detect mononuclear phagocytes infected with *Chlamydia, Helicobacter* or a Herpes virus to provide information useful for diagnosis or prognosis of vascular disease, such as atherosclerosis or arteriolosclerosis or coronary disease, such as congestive heart failure or susceptibility to myocardial infarction. Rather than identifying vascular disease, such as atherosclerosis, with invasive procedures by viewing the manifestations of fatty streaks, intermediate lesions, or fibrous plaques, this embodiment of the present invention provides information useful for determination of atherosclerosis or susceptibility to same using a minimally-invasive procedure by analysis of a blood sample, e.g., a peripheral blood sample. Determination of a change, especially an increase in the number of infected monocytes is important for a prognosis of disease since published epidemiological studies of vascular and coronary heart disease show at least a two-fold or larger odds ratio with the presence of infected monocytes. Some show increasing odds ratios with increasing antibody titres.

In another specific embodiment, the invention provides a unique method to detect and preferably quantitate the presence of an infectious agent such as *Chlamydia* in blood, spinal fluid or other body fluid. This information is particularly useful in determining the etiology of certain diseases or disorders of the central nervous system.

6. Exemplary Embodiment

The following non-limiting example illustrates the detection of *Chlamydia pneumoniae* infected mononuclear phagocytes to provide information useful for prognosticating atherosclerosis susceptibility. In this example, a peripheral blood sample is obtained from a patient suffering from at least one of the signs and symptoms of atherosclerosis. Using the automated image analysis method of the present invention, quantitative determination is made of the extent of *Chlamydia* infection of the patient's monocytes. Based on the information provided, a determination can be made regarding whether or not a course of treatment with antibiotic(s) effective against *Chlamydia* would be useful for ameliorating or preventing progression of at least one symptom or sign of atherosclerosis.

6.1. Smear Preparation

A non-coagulated whole blood sample is subjected to centrifugation through a Ficoll-Histopaque density gradient. The fraction containing mononuclear phagocytes is collected and washed with phosphate-buffered saline. Smears are prepared from aliquots of cells on glass microscope slides.

6.1.1. Cell Fixation

Smears are fixed in methanol for 5-10 minutes. Alternatively, smears may be fixed in ice-cold 0.05% glutaraldehyde for 10-30 minutes at room temperature. The smears are then washed with phosphate-buffered saline containing 0.1% bovine serum albumen.

6.1.2. Cell Staining

Staining for *C. pneumoniae* infected mononuclear phagocytes entails incubating the cells with fluorophore-conjugated genus-specific anti-Chlamydial monoclonal antibody for 15-60 minutes at room temperature in the dark. For example, ChlamydiaCel (available from CelLabs, Sydney, Australia) can be used. The smear then is counterstained with 4',6-Diamidino-2-phenylindole ("DAPI") for 5 minutes at room temperature. The smear is washed with phosphate-buffered saline and allowed to air dry.

6.2. Automated Smear Analysis

*C. pneumoniae* infected mononuclear phagocytes are identified to provide information useful to prognosticate atherosclerosis susceptibility. Automated image analysis of the smear is conducted as described in Section 5.1.1, supra. A description of the detailed method used in the exemplary embodiment follows.

6.2.1. Method

The PC executes a smear analysis software program compiled in MICROSOFT C++ using the MATROX IMAGING LIBRARY (MIL). MIL is a software library of functions, including those which control the operation of the frame grabber and which process images captured by the frame grabber for subsequent storage in PC as disk files. MIL comprises a number of specialized image processing routines particularly suitable for performing such image processing tasks as filtering, object selection and various measurement functions. The smear analysis software program runs as a WINDOWS 95 application. The program prompts and measurement results are shown on the computer monitor, while the images acquired through the imaging hardware are displayed on the dedicated imaging monitor.

6.2.2. Detection of the Signal

The *Chlamydia* infected mononuclear phagocyte detection algorithm is illustrated in the flow charts of FIGS. 2 and 3, where possible cell positions are identified at 1000.times. total magnification. The 100.times. objective is selected and the search for *C. pneumoniae* infected mononuclear phagocyte is conducted:

An optical field is selected and the microscopic image is acquired and transferred to the computer as an RGB image (201).

The Red component of the RGB image is transferred to a new monochrome grey-level image and clipped for pixel values of less than 50 to cut down signal noise (202).

The grey-level image is transformed to a binary image, a black and white image in which pixels with corresponding pixels in the Luminance image having grey-level values lower than the cut off point are set to 255 (white) (203).

An opening filter, successive applications of an erosion filter followed by a dilation filter, is applied for the removal of small noise particles from the binary image (204).

Application of a hole filling function fills the holes in the identified images (204). In this illustrative example, the hole filling function is commercially available as a MATROX function from Matrox (Montreal, Canada).

The area of each image is measured and all images having an area of 1000 pixels or greater are representative of mononuclear phagocytes. Cell images that have an area less than 1000 pixels are excluded from further processing (205).

The area, in pixels, of the cell images, i.e., mononuclear phagocytes, is recorded and saved for further processing (206).

The original Red component from the original RGB image is transferred to a binary image, so that pixels having grey-level values less than 200 are set to 0 while all the rest are set to 255 (207*a*).

The original Green component is transferred to grey level image (207*b*).

All pixels that have a value of 255 and any grey-level value in the Green component of the original RGB image form a new grey-level image (208).

This new grey-level image is transformed into a binary image where pixels that have grey-level values less than 100 are set 0 and the rest of the pixels are set to 255 (209).

The monocyte can be counted and recorded as an uninfected or *Chlamydia*-infected monocyte (210-212), or An opening filter is applied to remove small noise particles from the binary image (214).

The total area of the remaining cell images, which represents the total area of *Chlamydia* organisms with in the cell perimeter, is recorded. (215).

Percent area of each mononuclear phagocyte that is occupied by *Chlamydia* organisms can be calculated (216).

As further illustrated in FIG. 2, all optical fields on a slide can be assessed (FIG. 2, 217-118). The algorithm is repeated for additional fields of the smear according to the flow chart of FIG. 3. After *Chlamydia* infected mononuclear phagocytes are identified and quantified, the quantitative information is used, in combination with other relevant information regarding the physical and physiological state of the patient's vascular system to determine whether a course of antibiotic treatment is indicated for the patient.

Computer and image processing technologies are constantly changing. Newer technologies which meet the needs of the above-described methods and apparatus, while not specifically described here, are clearly contemplated as within the invention. For example, certain conventional pixel and image file formats are mentioned above, but others may also be used. Image files may be compressed using JPEG or GIF techniques now known in the art or other techniques yet to be developed. Other color spaces may also be used, as desired by the skilled artisan, particularly when detection of a sought-after characteristic is enhanced thereby.

The present invention has now been described in connection with a number of particular embodiments thereof. Additional variations should now be evident to those skilled in the art, and are contemplated as falling within the scope of the invention.

All references cited herein are incorporated herein by reference in their entirety.

What is claimed is:

1. A computer software product, comprising a non-transitory computer-readable storage medium having fixed therein a sequence of instructions which, when executed by a computer, direct the performance of a method for transforming an image into quantitative information regarding the extent of infection which comprises:
   acquiring an image of a specimen comprising host cells that have been treated to produce a first signal, infected by an infectious agent that has been treated to produce a second signal, said image comprising pixels each having a known area;
   performing image processing to remove noise artifacts from said image;
   identifying and determining quantity of pixels representing said host cells by detecting said first signal;
   identifying and determining quantity of pixels representing said infectious agent by detecting said second signal
   calculating infected area percentage by dividing said quantity of said pixels representing said infectious agent said quantity of said pixels representing said host cells to determine infected area percentage; and
   outputting said infected area percentage as quantitative information regarding extent of infection.

2. The computer software product of claim 1, wherein said infection agent of interest is a bacterium, mycoplasma, rickettsia, a spirochete, a fungus, a protozoal parasite, a virus or a prion.

3. The computer software product of claim 2, wherein said infection agent of interest is *Chlamydia* sp.

4. The computer software product of claim 2, wherein said infection agent of interest is *Borrelia* sp.

* * * * *